Figure 1:
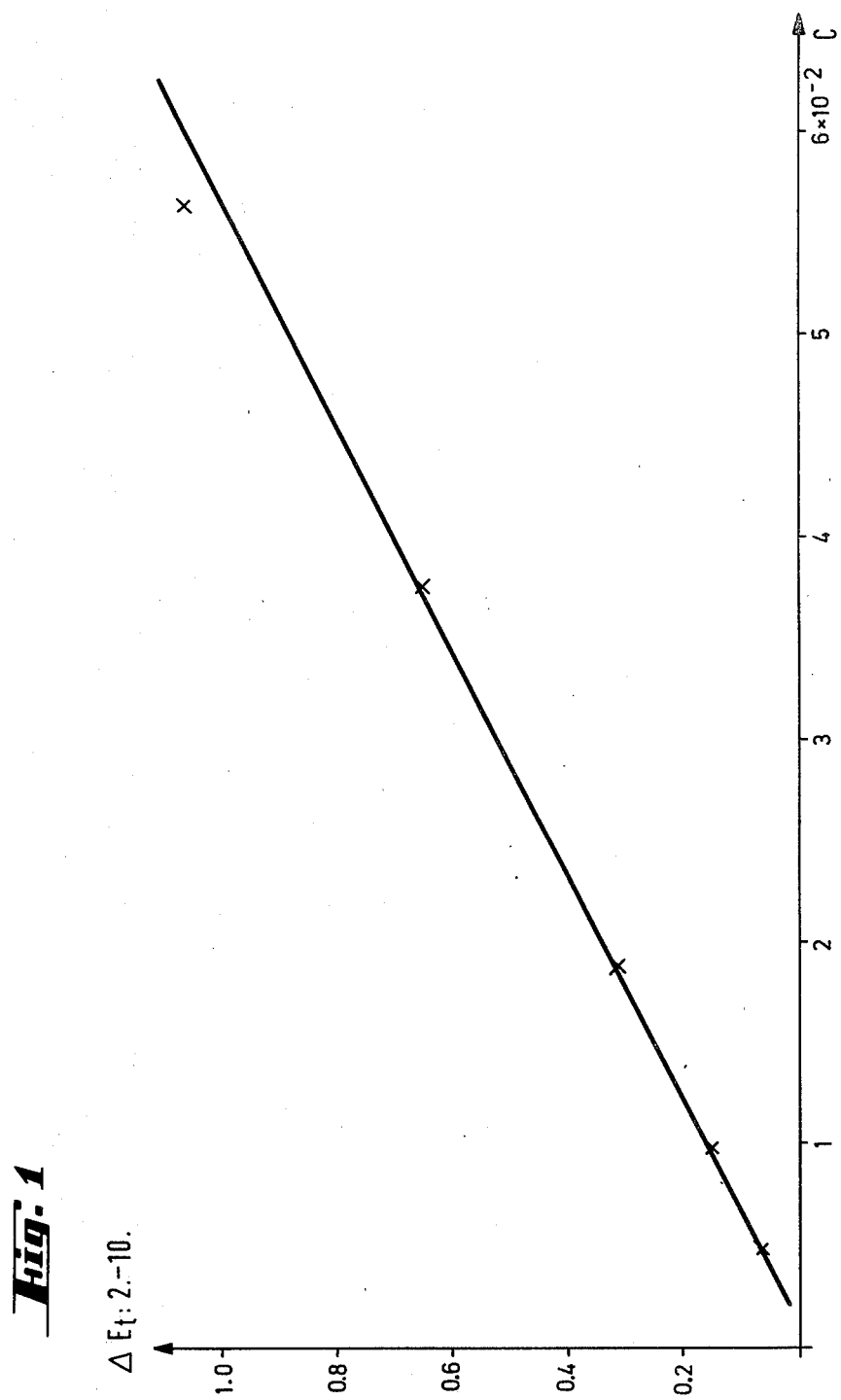

United States Patent [19]

Ziegenhorn et al.

[11] 4,409,328

[45] Oct. 11, 1983

[54] METHOD AND REAGENT FOR THE DETERMINATION OF GLYCEROL

[75] Inventors: Joachim Ziegenhorn, Starnberg; Knut Bartl, Wilzhofen; Albert Röder, Seeshaupt; Gunter Lang; Hans Möllering, both of Tutzing; Ulrich Nägele, Bernried, all of Fed. Rep. of Germany

[73] Assignee: Boehringer Mannheim GmbH, Mannheim-Waldhof, Fed. Rep. of Germany

[21] Appl. No.: 302,861

[22] Filed: Sep. 16, 1981

[30] Foreign Application Priority Data

Sep. 19, 1980 [DE] Fed. Rep. of Germany ....... 3035465

[51] Int. Cl.$^3$ .................. C12Q 1/26; C12Q 1/28; C12Q 1/30; C12Q 1/32; C12Q 1/44
[52] U.S. Cl. .................. 435/25; 435/19; 435/26; 435/27; 435/28; 435/805; 435/810
[58] Field of Search .............. 435/14, 18, 19, 25, 435/26, 27, 28, 805, 810

[56] References Cited

U.S. PATENT DOCUMENTS

| | | | |
|---|---|---|---|
| 3,362,886 | 1/1968 | Rupe | 435/14 |
| 3,367,842 | 2/1968 | Rupe et al. | 435/25 |
| 3,410,757 | 11/1968 | Fraser | 435/25 |
| 3,413,197 | 11/1968 | Fraser | 435/25 |
| 3,598,704 | 8/1971 | Dahlquist | 435/14 |
| 3,721,607 | 3/1973 | Gruber et al. | 435/28 |
| 3,838,011 | 9/1974 | Hager et al. | 435/25 |
| 4,202,941 | 5/1980 | Tenada et al. | 435/25 |
| 4,220,503 | 9/1980 | Johnson | 435/25 |
| 4,229,527 | 10/1980 | Ziegenhorn et al. | 435/25 |
| 4,273,870 | 6/1981 | Mollering et al. | 435/26 |

FOREIGN PATENT DOCUMENTS 2834705  1/1980  Fed. Rep. of Germany .

*Primary Examiner*—Esther M. Kepplinger
*Attorney, Agent, or Firm*—Felfe & Lynch

[57] ABSTRACT

For the determination of glycerol, the latter is incubated with galactose oxidase in an aqueous medium in the presence of oxygen and either the oxygen consumption or the amount of $H_2O_2$ or glyceraldehyde that is formed is determined. A reagent suitable for this purpose consists of galactose oxidase and a system for the determination of $H_2O_2$ or a system for the determination of glyceraldehyde. It can additionally contain an agent for the saponification of esterified glycerol.

27 Claims, 3 Drawing Figures

METHOD AND REAGENT FOR THE DETERMINATION OF GLYCEROL

The invention relates to a method for the enzymatic determination of glycerol and a reagent for the practice of this method.

The determination of triglycerides (=glycerol esters of long-chain fatty acids) is of considerable importance in medical diagnosis. An elevated triglyceride level in the blood is an important risk factor in regard to arteriosclerosis. When triglyceride levels are high, i.e., in hypertriglyceridemia, coronary insufficiency and myocardial infarction occur more frequently than they do at low triglyceride levels. Hypertriglyceridemia favors the occurrence of arteriosclerosis and coronary artery diseases and must therefore be recognized early so that treatment can begin in good time. A quick and reliable method for the determination of triglycerides or glycerol is therefore of great importance.

The known and useful methods for the determination of triglycerides are based on the enzymatic hydrolysis of the triglycerides by means of lipase and esterase and determination of the liberated glycerol by means of glycerokinase, pyruvate kinase and lactate dehydrogenase (A. W. Wahlefeld, in Methods of Enzymatic Analysis, IV, edited by H. U. Bergmeyer, Academic Press, New York, London, 1974, pp. 1831–1835).

This known method, however, has important disadvantages. In order to eliminate turbidity and trouble due to inherent serum coloring (bilirubin, hemoglobin) sample blank determinations must be performed, which increases the amount of time required per analysis as well as reagent consumption and hence cost. Furthermore, due to the presence of numerous sensitive coenzymes and enzymes, the keeping qualities of the prepared solutions are relatively poor.

In addition to this ultraviolet test, color tests are known which are based on the formation of formazane. The latter do permit determination against a reagent blank value, but they are relatively complicated and subject to error.

Finally, a method is known which uses a glycerol oxidase which forms $H_2O_2$ and glyceraldehyde, which can be determined. This enzyme, however, is obtained from highly pathogenic microorganisms, such as plaque bacilli, or can be obtained from other microorganisms only in very small yields.

There is, therefore, a need for a method and a reagent which does not have the disadvantages described above. In particular there is need for a method which can be practiced with an enzyme which is easy to obtain in good yield, and which will give sufficiently accurate results even without measurement against sample bank values. In particular, such a reaction, as an indicator reaction, must be able to use a color reaction in which the dye that is formed will have a sufficiently great extinction coefficient ($\epsilon > 18$ cm$^2$/$\mu$mol).

This object is achieved in accordance with the invention by a method for the determination of glycerol, which consists in incubating glycerol in an aqueous medium with galactose oxidase and either determining the oxygen consumption or the $H_2O_2$ or the glyceraldehyde that has formed.

Galactose oxidase EC 1.1.3.9 is a known enzyme which in the presence of oxygen oxidizes D-galactose to D-galactose hexodialdose and $H_2O_2$. It is a copper-containing enzyme. The invention is based on the surprising ascertainment that this enzyme can be readily used for the quantitative determination of glycerol. This was not to be expected, because although galactose oxidase (hereinafter called gal-OD) was known to have a minimal activity on glycerol, but the transformation rate with respect to galactose amounts to only one 150th according to Hamilton et al., in "Oxidases and Related Redox Systems", ed. King, Vol. 1 (1971). Since galactose also can occur in free or bound form in the body fluids in which it is desired to perform the glycerol determination, an unacceptably great interference from galactose was to have been expected, quite aside from the fact that, according to the known findings, a quantitative transformation of the glycerol was not foreseeable. Surprisingly, however, it has been found that in body fluids, and especially in serum, this undesirable interference is not encountered.

The method of the invention can be practiced also with prior or simultaneous enzymatic saponification of triglycerides with the release of glycerol, or with prior chemical saponification of triglycerides. Alcoholic potash lye, for example, is suitable for chemical saponification, and lipase with esterase or esterase alone for enzymatic saponification.

The measurement of oxygen consumption, $H_2O_2$ formation or glyceraldehyde formation can be performed by known methods for the purpose.

Suitable methods for the determination of oxygen consumption are, for example, gas chromatography and depolarization methods. Polarimetric determination with an oxygen electrode is preferred, since this method is particularly suitable for the automatic performance of the determination. Such determination methods are known. The methods described in German Offenlegungsschrift Nos. 2,130,340 and 2,130,308 for the polarimetric measurement of oxygen consumption in aqueous media have proven to be especially suitable.

The hydrogen peroxide that forms can be determined not only by titration but also by potentiometry, polarography and colorimetry as well as by enzymatic methods. Preferred are the enzymatic methods using catalase or peroxidase, since these are not only extremely specific and reliable, but they also can be combined in an extremely simple manner with the principal reaction with the formation of hydrogen. Determination by means of catalase in the presence of betadiketones such as acetyl acetone and methanol or ethanol or methylene glycol has also proven appropriate, as well as determination by means of peroxidase in the presence of one or more chromogens.

In determination by means of catalase, acetyl acetone and methanol, the latter is oxidized to formaldehyde which enters into a color reaction with acetyl acetone, and the color reaction can be measured. In determination by means of peroxidase, compounds are used as chromophores which can be determined photometrically after the reaction. One example of a suitable chromophore is 2,2'-aminobenzothiazoline sulfonic acid (ABTS). Another example is the indicator system described by Trinder (Ann. Clin. Biochem. 6 (1969), 24–27), in which phenol and 4-aminoantipyrine (4-AAP) are oxidatively coupled in the presence of POD and under the action of $H_2O_2$ to form a dye. Other aromatic alcohols, such as p-chlorophenol, aniline derivatives, naphthol, naphthol derivatives, naphthylamine, naphthylamine derivatives, aminoquinolines, hydroxyquinolines, dihydroxyphenylacetic acid and similarly reacting substances can be used instead of phenol. Instead of 4-aminoantipyrine, 4-aminoantipyrine derivatives such as 4-aminoantipyrinamide, phenylenediamine sulfonic acid, MBTH (methylbenzothiazolonehydrozone) S-MBTH (sulfonated methylbenzothiazolonehydrazone), MBTH and S-MBTH derivatives, as well as similarly reacting compounds can be used.

The determination of glyceraldehyde is performed by means of aldehyde reagents, preferably a hydrazine derivative reacting with aldehyde groups to form hydrazone, such as for example 2,4-dinitrophenylhydrazine. The hydrazone that is formed can then be determined colorimetrically.

The reaction in the presence of peroxidase and a chromogen, such as ABTS, is especially suitable and therefore preferred in the scope of the invention. A linear relationship between the extinction difference and the glycerol concentration has been found, even in the case of brief reaction times, so that this embodiment of the method of the invention is especially suitable for kinetic determination, though it is also usable for end point determinations.

The proportionality achieved between extinction and glycerol content is represented in FIG. 1 of the appended drawing. FIG. 1 is a graphic representation of the relationship between extinction and glycerol content.

According to a preferred embodiment of the invention, the determination is performed in the presence of glycerol dehydrogenase and its coenzyme NAD. Glycerol dehydrogenase EC 1.1.1.6 is known and can be obtained, for example, from microorganisms such as *Enterobacter aerogenes*, and it is commercially available. It has been found that in the presence of glycerol dehydrogenase (glyc-DH) the sensitivity and specificity of the determination method is still further improved. In this preferred embodiment of the invention, NAD can be added in an excess above the stoichiometrically necessary amount, but preferably only catalytic amounts of NAD are added, and an NAD-regenerating system. Suitable NAD-regenerating systems are described, for example, in German Offenlegungsschrift No. 2,834,705. A preferred NAD-regenerating system for use within the framework of the invention consists of lactate dehydrogenase and its substrate pyruvate. If an excess of NAD is used, it is possible to measure reduced NAD by optical methods instead of measuring the $H_2O_2$.

In this embodiment of the invention, the pH should be adjusted between 7.0 and 9.0, since in this range all of the participating enzymes, i.e., galactose oxidase (gal-OD), glyc-DH and peroxidase (POD) if used, have an activity that is well suited for the process.

Surprisingly, the reaction in this embodiment progresses smoothly and quantitatively, with the consumption of molecular oxygen and the formation of $H_2O_2$, although the two enzymes gal-OD and glyc-DH compete for the glycerol and the glyc-DH neither consumes oxygen nor forms $H_2O_2$.

By the preferred combined use of gal-OD and glyc-DH, the sensitivity range is extended down to at least 0.001 mol/l.

Figure 3:
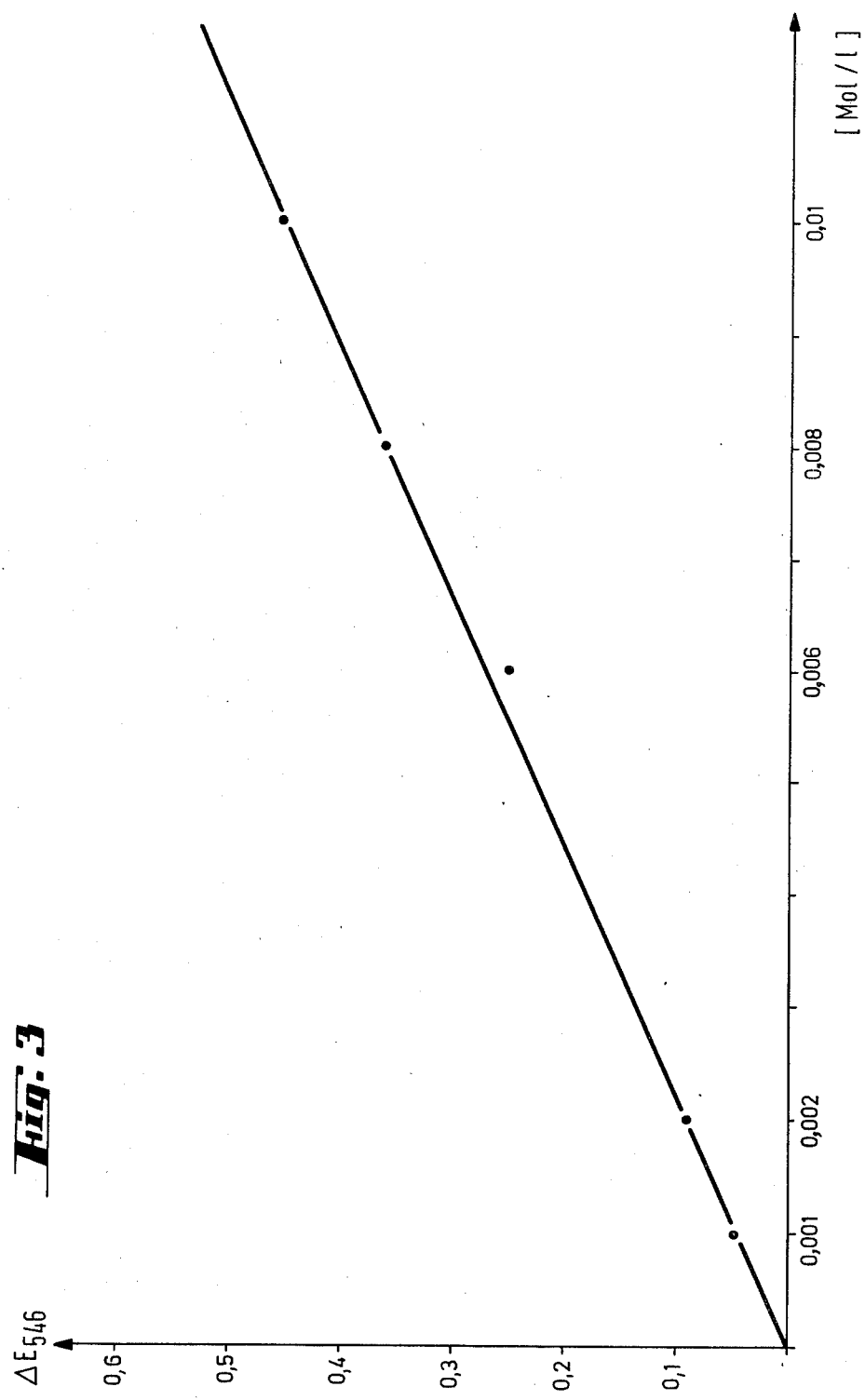

The measurement can be performed either by the end value method against a reagent blank value or by the kinetic method. FIG. 3 of the appended drawing shows that also in the case of the latter embodiment, there is a linear relationship between glycerol concentration and extinction difference at least down to glycerol concentrations of 0.0005 mol/l.

This embodiment of the method of the invention can also be performed with the simultaneous enzymatic saponification of triglycerides, wherein glycerol is released and is immediately determined in accordance with the invention.

The method is therefore especially suitable also for automatic analyzers, since the glycerol concentration can be determined precisely by calibration with a single standard.

Also subject matter of the invention is a reagent for the determination of glycerol, which consists of galactose oxidase and a system for the determination of $H_2O_2$ or a system for the determination of glyceraldehyde. In a first preferred embodiment, this reagent consists essentially of galactose oxidase, peroxidase, at least one chromogen, and buffer, individually or mixed. ABTS is preferred as the chromogen. Another preferred color indicator system is Trinder's system.

In another preferred embodiment, the reagent consists essentially of galactose oxidase, catalase, acetyl acetone, methanol and buffer, individually or mixed.

In an additional preferred embodiment, the reagent of the invention consists essentially of galactose oxidase and a hydrazine derivative reaction with aldehyde groups to form hydrazone, and a buffer. 2,4-dinitrophenylhydrazine is preferred as the hydrazine derivative.

The preferred reagent combinations mentioned above can contain, in addition to the stated essential components, conventional solvents, stabilizers and/or surface active substances. All these additives are known to the skilled practitioner of the art and commonly used in systems for the detection of hydrogen peroxide or glyceraldehyde. Preferably the reagents of the invention additionally contain lipolytic enzymes, such as lipase and esterase, or esterase alone, so that they can also be used for the determination of bound glycerol that is present in the form of triglycerides.

Preferably, the above-mentioned reagent combinations contain the essential components in the following ratios:

(1) 15 to 30 U/ml of galactose oxidase
    0.5 to 100 U/ml of peroxidase
    0.05 to 20 $\mu$mol/ml of chromogen
    plus, if desired,
    0.001 to 0.1 g/ml of surface active agent and
    buffer, pH 6 to 9;

(2) 15 to 30 U/ml of galactose oxidase
    1 to 10 $\mu$mol/l of 2,4-dinitrophenylhydrazine plus,
    if desired,
    0.001 to 0.1 g/ml of surface active agent and
    buffer, pH 6 to 9.

In a preferred embodiment, the reaction of the invention additionally contains glyc-DH, NAD and, if desired, an NAD-regenerating system.

The statements made above concerning the method apply in like manner to the NAD-regenerating systems. The preferred NAD-regenerating system consists of lactate dehydrogenase (LDH) and pyruvate. The presence of the NAD-regenerating system makes it possible to use no more than a catalytic amount of the NAD coenzyme for the glyc-DH, because NADH formed in the course of the reaction is immedially reoxidized back to NAD by the regenerating system. If such an NAD-regenerating system is present, therefore, the amount of NAD can amount to as little as 0.05 $\mu$mol/ml.

In this preferred embodiment of the reagent of the invention, the quantity of glyc-DH can best amount to from 5 to 100 U/ml. Of course, larger amounts can be used, but this is less economical. Amounts under 5 U/ml are usable, but then the advantages achieved by the glyc-DH are no longer obtained to the full extent.

Suitable buffers can be found by simple preliminary experiment. Potassium phosphate buffers, glycylglycine buffers and bicine (N,N-bis(2-hydroxyethyl)-glycine) buffers have proven useful in concentrations between 0.05 and 0.2 mol/l. The above-stated units of enzyme for galactose oxidase relate to galactose as substrate, as described, for example, by Pazur et al. in "Carbohydrates, Nucleosides, Nucleotides" 4, 147 (1977).

The following examples further explain the invention:

EXAMPLE 1

Samples:
Aqueous glycerol solutions
Reagent:
Potassium phosphate buffer (0.1 mol/l, pH 7.5), peroxidase (12,500 U/l), galactose oxidase (20,000 U/l), ABTS (2 mmol/l).
Sample:
Aqueous glycerol solution in the range of 0.005 to 0.06 mol/l.
Set-up for determination:
Measurement radiation:
Hg 405 nm; thickness of the layer in the cup: 1 cm, incubation temperature: 25° C.
Pipette 2.0 ml of reagent into the cup, add 0.1 ml of sample, and mix. Record change of extinction from the second to the tenth minute ($\Delta E_{2nd\text{-}10th}$). For the quantitative determination of glycerol, this $\Delta E$ is related to the glycerol concentration via a standard.

EXAMPLE 2

Figure 2:
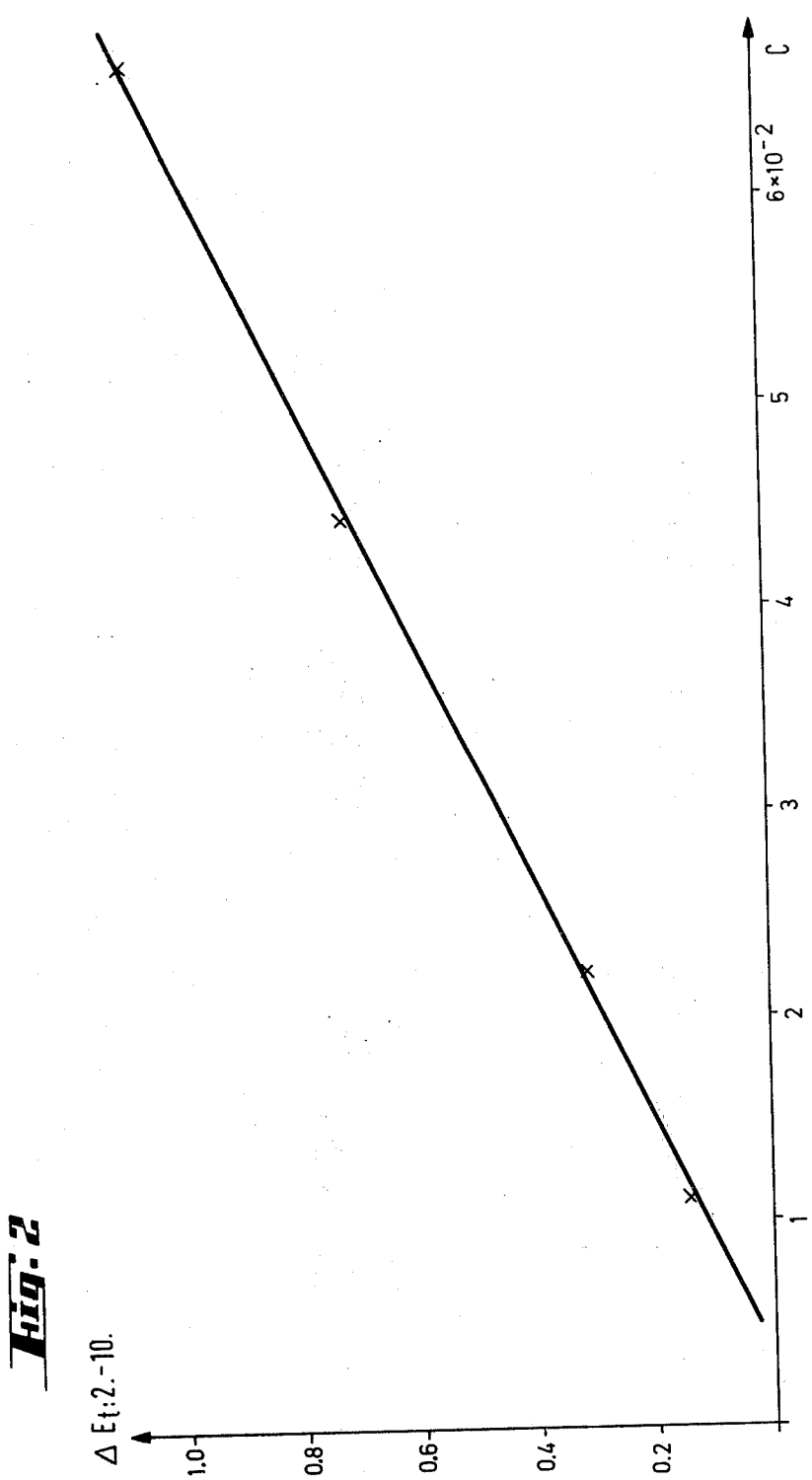

Determination of glycerol in serum
Reagent:
Potassium phosphate buffer (0.1 mol/l, pH 7.5), peroxidase (12,500 U/l), galactose oxidase (20,000 U/l), ABTS (2 mmol/l)
Sample:
The sample is serum to which various amounts of glycerol were added, ranging from 0.006 to 0.07 mol/l.
Set-up for determination:
Measurement radiation:
Hg 405 nm; thickness of the layer in the cup: 1 cm; incubation temperature: 25° C.
Pipette 2.0 ml of reagent into the cup, add 0.1 ml of sample and mix. After the end of the lag phase the extinction change is recorded from the second to the tenth minute. The linear relationship between the glycerol concentration and the extinction change is shown in FIG. 2 of the drawing.

EXAMPLE 3

| Reagent: | | |
|---|---|---|
| Glycylglycine buffer, pH 8.0; | 0.1 mol/l |
| (NH4)2SO4 | 0.16 mol/l |
| ZnSO4.7H2O | 0.1 mmol/l |
| Na2CO3 | 0.078 mol/l |
| 4-aminoantipyrine-NH2 | 0.5 mmol/l |
| p-chlorophenol | 10 mmol/l |
| POD | 10,000 U/l |
| LDH | 10,000 U/l |
| pyruvate | 2.5 mmol/l |
| gal-OD | 20,000 U/l |
| glyc-DH | 50,000 U/l |
| NAD+ | 1.5 mmol/l |

Sample:
Aqueous glycerol solutions ranging from 0.001 to 0.01 mol/l (Instead of the aqueous glycerol solutions, serum or other body fluids and even, for example, food extracts can be used).
Set-up for measurement:
Measurement radiation: 546 nm
Thickness of layer in cup: 1 cm
Temperature: 25° C. to 37° C.
Place 1.0 ml of reagent in the cup and start with 0.01 ml of sample. Measure extinction after 30 minutes against the reagent blank value. For the quantitative determination, this $\Delta E$ is related to the glycerol concentration via a standard.

It is not necessary to include a sample blank value. A curve obtained by plotting the glycerol concentration against the extinction at 546 nm is given in FIG. 3.

We claim:
1. Method for the determination of glycerol, comprising the steps:
incubating glycerol with galactose oxidase in an aqueous medium in the presence of oxygen for a time and under conditions sufficient for a reaction to occur; and
measuring the oxygen consumed or the products produced in the reaction as a measure of the glycerol.
2. The method of claim 1 wherein oxygen consumption is determined.
3. Method of claim 2 wherein the oxygen consumption is determined by polarography.
4. The method of claim 1 where $H_2O_2$ formation is measured as the product produced.
5. The method of claim 4 wherein $H_2O_2$ is measured enzymatically with catalase or peroxidase.
6. The method of claim 5 wherein peroxidase and a chromogen are added and the coloration or change of extinction is determined.
7. The method of claim 2 or 4 wherein the measurement is performed kinetically in a predetermined brief interval of time.
8. The method of claim 1 wherein glycerinaldehyde formation is measured as the product produced.
9. Method of claim 8 wherein the glycerinaldehyde is measured by reaction with a hydrazine derivative to form the corresponding hydrazone, the corresponding hydrazone being measured.
10. Method of claim 1 wherein glyceroldehydrogenase and NAD are added to the incubation.
11. Method of claim 10 wherein NAD is added together with an NAD-generating system.
12. The method of claim 11 wherein pyruvate and lactate dehydrogenase are used as the NAD-regenerating system.
13. Method of claim 10 wherein reduced NAD is determined.
14. Method of claim 1 wherein the incubation is performed at a pH of 7.0 to 9.0.
15. A reagent for the determination of glycerol by the method of claim 1, comprising galactose oxidase; a system for the determination of $H_2O_2$ or a system for the determination of glyceraldehyde, and an agent for the saponification of esterified glycerol.

16. The reagent of claim 15 including a system for the determination of $H_2O_2$, said system for the determination of $H_2O_2$ consisting of peroxidase, at least one chromogen, and buffer.

17. Reagent of claim 16 comprising 0.5 to 100 U/ml of peroxidase, 5 to 35 U/ml of galactose oxidase and 0.05 to 20 μmol/ml of chromogen.

18. Reagent of claim 17 containing 0.5 to 100 U/ml of glycerol dehydrogenase and at least 0.05 μmol/ml of NAD.

19. Reagent of claim 15 further containing glycerol dehydrogenase, NAD, and an NAD-regenerating system.

20. Reagent of claim 19 wherein the NAD-regenerating system consists of pyruvate and lactate dehydrogenase.

21. Reagent of claim 15 wherein the chromogen consists of p-chlorophenol and 4-aminoantipyranamide.

22. Reagent of claim 21 containing 5 to 15 μmol/ml of p-chlorophenol and 0.1 to 1.0 μmol/ml of 4-aminoantipyrinamide.

23. Reagent of claim 15 wherein the chromogen consists of 2,2'-azinodi-(3-ethylbenzothiazolinesulfonic acid-6)-diammonium salt.

24. Reagent of claim 15 further comprising glycylglycine buffer or bicine buffer, pH 7.0 to 9.0.

25. Reagent of claim 15 further comprising a surface active agent.

26. Reagent of claim 15 further comprising a support material on which the reagent is impregnated.

27. Reagent of claim 26 wherein said support material is a paper.

* * * * *